(12) United States Patent
Konishi

(10) Patent No.: US 6,541,041 B1
(45) Date of Patent: Apr. 1, 2003

(54) CRUDE DRUG EXTRACTS, AND METHODS FOR MAKING AND STANDARDIZING SAME

(75) Inventor: Jin-emon Konishi, Musashino (JP)

(73) Assignee: Nippon Zoki Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/492,118

(22) Filed: Jan. 27, 2000

Related U.S. Application Data

(62) Division of application No. 09/200,918, filed on Nov. 30, 1998.

(30) Foreign Application Priority Data

Nov. 28, 1997 (JP) .............................................. 9-344345

(51) Int. Cl.[7] .............................................. A61K 35/78
(52) U.S. Cl. ........................ 424/725; 424/724; 424/520
(58) Field of Search ............................. 424/195.1, 520, 424/724, 725

(56) References Cited

U.S. PATENT DOCUMENTS

| | | |
|---|---|---|
| 3,959,566 A | 5/1976 | Pangonis |
| 4,036,787 A | 7/1977 | Blount |
| 4,039,474 A | 8/1977 | Feistel et al. |
| 4,056,937 A | 11/1977 | Suzuki |
| 4,089,883 A | 5/1978 | Blount |
| 4,138,421 A | 2/1979 | Blount |
| 4,145,415 A | 3/1979 | Sato |
| 4,863,518 A | 9/1989 | Blount |
| 4,985,254 A | 1/1991 | Konishi et al. |
| 4,985,354 A | 1/1991 | Toyomaki et al. |
| 5,013,558 A | 5/1991 | Konishi |
| 5,057,324 A | 10/1991 | Shibayama et al. |
| 5,127,994 A | 7/1992 | Johansson |
| 5,227,089 A | 7/1993 | Hasegawa et al. |
| 5,534,509 A | 7/1996 | Konishi et al. |
| 5,560,935 A | 10/1996 | Konishi et al. |
| 5,658,896 A | 8/1997 | Konishi et al. |
| 5,767,103 A | 6/1998 | Greenberg et al. |
| 5,807,951 A | 9/1998 | Konishi et al. |

FOREIGN PATENT DOCUMENTS

| | | |
|---|---|---|
| EP | 0 315 591 A2 | 5/1989 |
| EP | 0 315 591 | 10/1989 |
| EP | 0341209 A2 | 11/1989 |
| EP | 0 348 353 A2 | 12/1989 |
| EP | 0 621 038 A1 | 10/1994 |
| EP | 0 645 142 A1 | 3/1995 |
| EP | 0 733 636 A1 | 9/1996 |
| FR | 2 610 523 | 8/1988 |
| FR | 2 671 488 | 7/1992 |
| GB | 697351 | 9/1953 |
| GB | 0 300 973 | 4/1989 |
| JP | 53-101515 | 9/1978 |
| JP | 57-77697 | 5/1982 |
| JP | 57-183720 | 11/1982 |
| JP | 58-35117 | 3/1983 |
| JP | 58-121217 | 7/1983 |
| JP | 63-25600 | 5/1988 |
| JP | 63-039572 | 8/1988 |
| JP | 3-43279 | 7/1991 |
| JP | 3-204803 | 9/1991 |
| JP | 2594222 | 12/1996 |
| JP | 62-145022 | 6/1997 |
| WO | WO 93/08828 | 5/1993 |

OTHER PUBLICATIONS

Boltz et al. Analytical Chemistry (1947), vol. 19, No. 11, pp. 873–877.*

Steranka et al., "Bradykinin as a pain mediator: receptors are localized to sensory neurons, and antagonists have analgesic actions." *Proc Natl Acad Sci USA*,, May 1988, 85(9):3245–9.

Galvez et al., "Antidiarrhoeic activity of Euphorbia hirta extract and isolation of an active flavonoid constituent." *Plant Med*, Aug. 1993, 59(4):33–6.

Hamada et al., "Free radical scavenging action of baicalein.", *Arch Biochem Biphys.*, Oct. 1993, 306(1):261–6.

Xu et al., "Immunological mechanisms of antitumor activity of some kinds of crude drugs on tumor necrosis factor production." *Int J Immunopharmacol*, 1989, 11(6):607–13.

Habib et al., "Difference spectrophotometric estimation of santonin", *J Assoc Off Anal Chem*, Sep.–Oct. 1984, 67(5):939–41.

Lin et al., "Medicinal plants used for the treatment of hepatitis in Taiwan", *Am J Chin Med*, 1990, 18(1–2):35–43.

Lin et al., "The anti–flammatory effects of Chinese crude drug prescriptions on experimental arthritis.", *Am. J. Chin Med*, 1995, 23(2):145–52.

Takeoka, Y. et al., "Influence of Neurotropin on Thymic Microenvironmental Abnormalities of NZB Mice," *Int. J. Immunotherapy*, XI(2), pp. 49–56 (1995).

"Drugs in Japan, Ethical Drugs," Yakugyo Jiho Co., Ltd., 1994, p. 1434.

(List continued on next page.)

Primary Examiner—Francisco Prats
Assistant Examiner—Susan D. Coe
(74) Attorney, Agent, or Firm—Hollander Law Firm, P.L.C.

(57) ABSTRACT

Crude drug extracts containing soluble silicon compounds as an effective component are obtained by subjecting a crude drug to extraction with water or an aqueous solvent, preferably at an alkaline pH. The crude drugs subjected to extraction to obtain the extracts may be derived from animals, plants, etc. The quality of the crude drug extract can be standardized using the soluble silicon compounds as an index. The soluble silicon compounds exhibit inhibitory action towards the production of plasma kallikrein. The amount of soluble silicon compounds in the dry extract may be used as an index whereby the quality of various crude drugs can be standardized which contributes to providing crude drug extracts having a stable or consistent quality. Consequently, the present invention greatly contributes to the appropriate standardization of pharmaceuticals.

13 Claims, No Drawings

OTHER PUBLICATIONS

Fujii, Y., et al., "Biological Overview of HIV Accessory Protein Nef," *Saibo Kogaku*, vo. 16, No. 1, pp. 94–99 (1997).

Section CH, Week 9645, Derwent Publications Ltd., Class B04, AN 96–450925 XP002109698 & JP 08225452 A, Sep. 3, 1996, abstract.

De Reuck J., et al., "A double–blind study of neurotropin in patients with acute ischemic stroke," *ACTA Neurologica Scandinavica* vol. 89, No. 5, 1994, pps. 329–335, XP002109696.

Yokoi et al., "Effect of Degree of Polymerization of Silicic Acid on the Gastrointestinal Absorption of Silicate in Rats," *Chem. Pharm. Bull.*, vol. 27, No. 8, 1979, pp. 1733–1739.

Derwent Publications Ltd., London, GB: AN 82–10241J, "Drug For Cultivated Fish," & JP A57183720 (Mitani J.), Nov. 12, 1982, abstract.

"Remedy For Burn," *Patent Abstracts of Japan*, vol. 7, No. 255 (C–189), Oct. 6, 1983, & JPA58121217 (Kagitani Takeo), Jul. 19, 1983, abstract.

Chemical Abstracts, vol. 106, No. 10, Mar. 9, 1987, Srivastava et al., XP002096181.

Patent Abstracts of Japan, vol. 017, No. 225 (C–1055), May 10, 1993 & JP 04360838.

Database WPI Section Ch, Week 9624, Derwent, XP002113090 & CN 1 096 180, Dec. 14, 1994, abstract.

Database BIOSIS, XP–002113089, Li S–Y, et al. Studies on the Protective Action of Silicon Compound of Equisetum Against Experimental Liver Injury in Rats and Mice & Zhongguo Yaolixue Yu Dulixue Zazhi. ISSN: 1000–3002, abstract.

Zhao C, et al., "Determination of water soluble silicon from herbal drugs", Chung Kuo Chung Yao Tsa Chih, vol. 15, No. 9, 1990, pps. 555–556.

Paslawska et al., "Studies on the Optimum Conditions of Extraction of Silicon Species from Plants With Water", Planta Medica, vol. 29, No. 1, 1976, pps. 72–79, & XP002113087.

Piekos et al., "Studies on the Optimum Conditions of Extraction of Silicon Species from Plants With Water", Planta Medica, vol. 27, 1975, pps. 145–150, XP002113088.

Database WPI, Section Ch, Week 9411, Derwent, XP002113091 & RU 2003338 C, Nov. 30, 1993, abstract.

Sprumont, et al., Morphometrical Quantification of Brian Edema Related to Experimental Multiple Micro–Infarcts in Mice: Assessment of Neurotropin Effect, *Meth Find Exp Clin Pharmacol* 1993, 15(3): 169–177, XP002109697.

"Drug for Food Poisoning," *Patent Abstracts of Japan*, vol. 11, No. 371 (C–462), Dec. 3, 1987 & JPA62145022 (Sofuto Shirika) Jun. 29, 1987, abstract.

"Adsorbent for Peroxylipid," *Patent Abstracts of Japan*, vol. 15, No. 474 (C–890), Dec. 3, 1991 & JPA3204803 (Shiscido Co., Ltd.) Sep. 6, 1991, abstract.

Patent Abstracts of Japan, vol. 014, No. 254 (C–0724), May 31, 1990 & JP 02073020, abstract.

The Merck Index, 9th ed. 1976, No. 7456, 8443, 8233–8243 & 5514–5515.

Wang et al., Mushroom Biology and Mushroom Products, Proc. Int. Conf. 2nd, Editor: Royse, Daniel J. Publisher: Penn State University, College of Agricultural Sciences, University Park, PA, 1996, pp. 205–206.

\* cited by examiner

CRUDE DRUG EXTRACTS, AND METHODS FOR MAKING AND STANDARDIZING SAME

This is a divisional of application Ser. No. 09/200,918 filed Nov. 30, 1998.

FIELD OF THE INVENTION

The present invention relates to crude drug extracts containing soluble silicon compounds as an effective component, methods for making the crude drug extracts, and also to standardization methods for crude drugs and their extracts.

BACKGROUND OF THE INVENTION

Living organisms conducting living phenomenon are composed of cells where functional abnormality in the cells introduces the living organisms to a diseased state. Living organisms survive as an individual by adjusting and maintaining their physical and chemical states to and within certain stable physiological conditions corresponding to changes in internal and external circumstances. It is well known that the maintenance and the normalization of the biofunction are especially carried out by various receptors on cell surfaces and the ion channels such as sodium, potassium, calcium, etc. However, if the above-mentioned biofunctions are unbalanced for some reason and it becomes chronic, so-called morbidity results causing various diseases.

The cell membrane consists of lipid bilayers and has an important and complicated function for maintenance of life such as selective permeability, active transport, generation of bioelectricity, expression of immunoactivity, etc. Although normal cells have fluidity and exhibit self-repairing ability to injury, the fluidity of the cell membrane decreases due to internal and external invasions. Exemplary of such invasions are aging, various diseases, and excessive stress stimulation including viral and bacterial infection. The invasions and consequent decrease in fluidity deteriorates maintenance of the homeostasis of a living body. For example, it is well known that vascular endothelial cells and nerve cells are injured by hyperlipemia, hypertension, diabetes mellitus, aging, smoking, etc. resulting in arteriosclerosis, renal diseases, peripheral nervous disorder, etc.

A known mechanism for adjusting the complicated functions in vivo, is an enzymatic system called the kallikrein-kinin system. With respect to this plasma kallikrein-kinin system, it is believed that a blood coagulation factor XII (a Hageman factor, abbreviated as FXII) is activated due to stimulation by a lesion or an invasion to the tissues in vivo whereby a series of enzymatic reactions is induced. Thus, the activated blood coagulation factor XII (abbreviated as FXIIa) acts on plasma prekallikrein which exists in the same plasma to convert it to plasma kallikrein which is an enzyme in activated form. Then, the plasma kallikrein acts on high-molecular-weight kininogen (abbreviated as HK) in the plasma to liberate bradykinin.

The bradykinin which is a product of the plasma kallikrein-kinin system exhibits various physiological activities such as dilation of peripheral blood vessels, acceleration of permeation of blood vessels, induction of pain, generation of inflammation, migration of leucocytes, etc. Bradykinin has also been known as a mediator for induction of pain, inflammation and allergic reactions. Accordingly, when an excessive liberation and production of bradykinin is inhibited, it is possible to relieve pain, inflammation, allergic syndromes, etc. and to make such unhealthy states normal.

The plasma kallikrein-kinin system acts in vivo having a close relationship with various other enzymatic reaction systems such as the renin-angiotensin system, the blood clotting system, the fibrinolysis system, the complement system as well as the catecholamine and arachidoic acid cascade mainly related to prostaglandins, leukotrienes and thromboxanes. Accordingly, the kallikrein-kinin system is closely related to blood pressure regulating action, action through the blood clotting-fibrinolysis-complement system or bioregulation and improving action for peripheral circulation by various physiologically active substances produced by the arachidoic acid cascade and plays an important role in the regulation of functions in vivo. Thus, the plasma kinin-kallikrein system basically relates to biofunctions and participates in various bioregulation systems. Therefore, it has been suggested that a substance having an effect on the plasma kinin-kallikrein system shows various pharmacological activities.

The present inventor has conducted a study, where a plasma kallikrein-kinin system is utilized, paying attention to silicon compounds which regulate immune action and autonomic action of nerve cells in living organisms. Silicon is widely distributed in the animal and vegetable kingdoms. Especially in animal tissues, it is abundantly present as silicic acid in skin, hair, bone and various organs such as the lung, adrenal gland, thymus, pancreas and spleen. Silicon is known to be an essential component for the formation of bones. Further, in animal tissues, silicic acid forms a collagen cross-linking chain and is contained as a constituting component of acidic mucopolysaccharides and it has been suggested that elasticity of skin is related to the amount of silicic acid.

Crude drugs have been used in medical treatment since ancient time but their quality has been mostly confirmed only by means of empirical extracting methods for many years. For example, in the methods of evaluating the quality of crude drugs in the Japanese Pharmacopoeia (13th Edition), many of the methods are merely a confirmation test by means of color reaction or spots in thin layer chromatography. Under such circumstances, there has been a strong demand for establishing a standardization for the substances so that a predetermined effect for the crude drug can be guaranteed. Standardization for quality of various crude drugs by means of a substantial index related to pharmaceutical effect would contribute to providing crude drug extracts having a stable quality and would greatly contribute to an appropriate standardization of pharmaceuticals.

The present inventor has studied silicon compounds in living organisms and regulated the quality of crude drugs using silicon compounds to express their pharmaceutical effect in vivo whereupon the present invention has been accomplished. The present invention provides crude drug extracts containing soluble silicon compounds as an effective component which exhibit inhibitory action against the production of plasma kallikrein. The present invention also provides methods for manufacturing crude drug extracts, and standardizing methods for crude drugs and extracts thereof.

SUMMARY OF THE INVENTION

A crude drug extract which inhibits production of plasma kallikrein may be produced by subjecting a plant or animal crude drug to extraction with water or an aqueous-based extracting solvent to obtain an extract having at least about 0.05 mg of at least one soluble silicon compound calculated as silicon per gram of dry extract, as an effective component.

In preferred embodiments, an alkaline extracting solvent is employed to substantially increase the soluble silicon compound content of the crude drug extract. The extracting solvent may have a pH of from about 8.5 to about 10.5. The reaction may be conducted at room temperature, or the extract may be heated or boiled, followed by evaporating the solvent therefrom to give a dry substance. Examples of aqueous-based extraction solvents include mixtures of water with ethanol or phenol. In embodiments of the invention, prior to extraction with the alkaline extracting solvent, the crude drug may be subjected to extraction with an extracting solvent having a neutral pH. The crude drug extracts of the present invention may be used in pharmaceutically effective amounts as an anti-allergic agent, an analgesic agent, or an anti-inflammatory agent to treat patients in need thereof.

Standardizing or evaluating animal or plant crude drugs for pharmaceutical effectiveness may be achieved by subjecting an animal or plant crude drug to extraction to obtain an extract solution, drying the extract solution to obtain a dry crude drug extract, determining the amount of soluble silicon compounds calculated as silicon per gram of dry crude drug extract, and comparing the determined amount of soluble silicon compounds to a minimal amount needed to obtain inhibition of plasma kallikrein production. In embodiments of the invention, standardizing crude drug extracts, such as plant crude drug extracts may be performed by determining the amount of soluble silicon compounds calculated as silicon per gram of dry crude drug extract, measuring inhibiting action of the crude drug extract against plasma kallikrein, and subjecting the crude drug extract to a plurality of coloring reactions.

DETAILED DESCRIPTION OF THE INVENTION

The present invention relates to crude drug extracts which contain not less than 0.05 mg of soluble silicon compounds calculated as silicon per gram of the dry crude drug. The crude drug extract of the present invention may be obtained by extraction of various crude drugs, for example, animal and plant crude drugs including tanjin (*Salviae militiorrhizae* radix), shireishi (*Ganoderma lucidum*), creeping saxifrage (*Saxifraga stolonifera*), scouring rush (*Equisetum hiemale*), Chinese gutta percha, plantago herb, plantago seeds, chorei (polyporus sclerotium), saiko (bupleurum root), Japanese angelica root, elderberry, bukuryo (poria sclerotium), pueraria root, crude aloe, ginseng, ginger, alisma rhizome, schisandra fruit, sanshiti (root of *Panax nothoginseng*), jujube, chinpi (citrus unshiu peel), bakumondo (ophiopogon tuber), young staghom, oriental bezoar, lumbicusa, bear bile, longgu, etc. The present invention is applicable to any crude drug extract derived from animals, plants, minerals, etc. satisfying the requirements of the present invention. Such crude drug materials are extracted with water, ethanol or a suitable extracting solvent to which an additive such as phenol is added whereby the crude drug extract can be manufactured. At that time, extraction and concentration of the active substances may be enhanced by heating or changing the pH of the solvent. Thus, the following manufacturing methods may be exemplified for obtaining crude drug extracts in accordance with present invention:

1) Pure water is added to a crude drug material, the mixture is boiled with stirring and the insoluble matters are removed by filtration or the like to give an extract solution. The extract solution is concentrated if necessary and spray-dried or freeze-dried in vacuo to give a powder.

2) Pure water is added to a crude drug material, the mixture is boiled with stirring and the insoluble matters are removed by filtration or the like to obtain an extract. Pure water is further added to the residue, pH is adjusted to an alkaline region (to 8.5–10.5, for example to around 9.5), then the mixture is boiled with stirring again, and the insoluble matters are removed by filtration or the like to obtain an extract, and the extract is adjusted to about the neutral pH region and combined with the already-prepared first extract. Then, the combined extract is concentrated and/or evaporated to dryness if necessary to give a powder. Spray-drying or freeze-drying in vacuo to give a powder may be employed as in the above-mentioned method 1).

3) To a crude drug material is added a 1% aqueous phenol solution followed by boiling with stirring and the insoluble matters are removed by filtration or the like to give an extract solution. The extract solution is concentrated if necessary and spray-dried or freeze-dried in vacuo to give a powder.

4) Pure water and ethanol are added to a crude drug material, the mixture is boiled with stirring and the insoluble matters are removed by filtration or the like to give an extract solution. The extract solution is concentrated if necessary and spray-dried or freeze-dried in vacuo to give a powder.

5) After conducting the extracting operations as described in the above methods 1) to 4), the pH of the extract is adjusted to weakly alkaline (for example, to pH of around 8.5) followed by concentrating, and the pH of the concentrate is adjusted to nearly the neutral region followed by pulverizing in the same manner as mentioned above.

Conventional pH adjusting agents, such as inorganic or organic bases and acids and salts may be employed to obtain a desired pH for the extracting solvent and extract. For example, alkali metal hydroxides such as sodium hydroxide, and potassium hydroxide, etc. may be employed to obtain a desired alkaline pH. Exemplary acids which may be employed to adjust pH to the neutral range include hydrochloric acid, sulfuric acid, and hydrobromic acid, etc.

In accordance with the present invention, crude drug extracts are characterized and evaluated for pharmaceutical effectiveness by specifying the soluble silicon compound content of the crude drug extract. The content of the soluble silicon compounds in the dried crude drug extract obtained by the above-mentioned manufacturing methods can be analyzed by the following method and is able to be regulated as an amount calculated as silicon.

Thus, the crude drug extract is added to water (to an extent of 1 mg/ml), the mixture is subjected to stirring and an ultrasonic treatment. In preferred embodiments, the stirring is conducted at room temperature for about ten minutes and ultrasonic treatment is conducted at room temperature for about ten minutes. Then, the insoluble matters are removed by filtration or centrifugation, and the amount of silicon in the resulting solution is measured by a molybdenum blue method. In addition, an inhibiting action of the same sample solution against the production of plasma kallikrein is measured and is confirmed as an index for the soluble silicon compounds. The measured inhibiting action against plasma kallikrein production is important as an index for the measurement and confirmation of the titer (potency of the biological activity) of the soluble silicon compounds having a biological activity.

In addition to the crude drug extract in which the soluble silicon compounds are specified, the present invention further covers various embodiments such as a method of manufacturing the same and its pharmaceutical use. Preferred embodiments of the present invention are:

(1) A crude drug extract containing 0.05 mg or more soluble silicon compounds (calculated as silicon) per gram of the dry substance.

(2) A crude drug extract according to the above paragraph (1) which is extracted from one of the animal and plant crude drugs selected from the group consisting of tanjin (*Salvia militiorrhiza* radix), shireishi (*Ganoderma lucidum*), creeping saxifrage (*Saxifraga stolonifera*), scouring rush (*Equisetum hiemale*), Chinese gutta percha, plantago herb, plantago seeds, chorei (polyporus sclerotium), saiko (bupleurum root), Japanese angelica root, elderberry, bukuryo (poria sclerotium), pueraria root, crude aloe, ginseng, ginger, alisma rhizome, schisandra fruit, sanshiti (root of *Panax nothoginseng*), jujube, chinpi (citrus unshiu peel), bakumondo (ophiopogon tuber), young staghorn, oriental bezoar, lumbicusa, bear bile, longgu, etc.

(3) A crude drug extract according to the above paragraph (1) which is extracted from one of the crude drugs selected from the group consisting of tanjin (*Salvia militiorrhiza* radix), shireishi (*Ganoderma lucidum*), creeping saxifrage (*Saxifraga stolonifera*), scouring rush (*Equisetum hiemale*), Chinese gutta percha, plantago herb, plantago seeds, chorei (polyporus sclerotium), saiko (bupleurum root), Japanese angelica root, elderberry, bukuryo (poria sclerotium), pueraria root, crude aloe and ginseng.

(4) A crude extract according to the above paragraph (1), (2) or (3) in which water is added to the dry substance (to an extent of 1 mg/mL) and the amount of the silicon compounds existing in a solubilized state in said aqueous solution is regulated or specified.

(5) A method for the manufacture of a crude drug extract according to any one of the above paragraphs (1) to (4) in which an extracting solvent where the pH is adjusted to an alkaline region is used.

(6) A manufacturing method according to the above paragraph (5) in which an extracting solvent where the pH is adjusted to from 8.5 to 10.5 is used.

(7) A method for the manufacture of a crude drug extract according to any one of the above paragraphs (1) to (4) in which an extraction is conducted using an extracting solvent near the neutral pH region (pH of about 7), followed by using an extracting solvent where the pH is adjusted to an alkaline region, such as a pH of from 8.5 to 10.5.

(8) A manufacturing method according to any of the above paragraphs (5) to (7) in which the crude drug material is extracted by heating or boiling followed by evaporating the solvent therefrom to give a dry substance.

(9) A manufacturing method according to any of the above paragraphs (5) to (8) in which water, ethanol or a mixed solution thereof is used as an extracting solvent.

(10) A manufacturing method according to the above paragraph (9) in which an extracting solvent to which an additive such as phenol is added is employed.

(11) A method for the standardization of a crude drug extract in which soluble silicon compounds are used as an index.

(12) A method according to the above paragraph (9) in which a crude drug mentioned in paragraph (2) or (3) is standardized.

(13) A method according to the above paragraph (12) in which the crude drug is standardized by a method according to paragraph (4) above.

(14) A method according to any of the above paragraphs (11) to (13) in which the crude drug is standardized by combining identifying tests such as a coloring reaction.

(15) An inhibiting agent against plasma kallikrein production containing a crude extract according to any of paragraphs (1) to (4) above as an effective component.

(16) An inhibiting agent against plasma kallikrein production according to the above paragraph (15) in which said agent is an anti-allergic agent.

(17) An inhibiting agent against plasma kallikrein production according to the above paragraph (15) in which said agent is an analgesic agent.

(18) An inhibiting agent against plasma kallikrein production according to the above paragraph (15) in which said agent is an anti-inflammatory agent.

An extract of a crude drug of the present invention can be used as a drug material in extract form or a dried powder form. The crude drug extract can be made into pharmaceutical preparations as is without any excipients or together with commonly-used excipients. For example, a crude drug extract which is an effective component of the pharmaceutical compositions of the present invention can be made into various pharmaceutical compositions or preparations by combining one or more of the extracts with at least one pharmaceutical carrier or diluent. The extracts can be made into various types of preparations by known methods. The pharmaceutical preparations or compositions may be made into solid, semi-solid, liquid or aerosol formulations for oral administration (e.g. tablets, capsules, powders, liquids, etc.) and for parenteral administration (e.g. for subcutaneous, intravenous, intramuscular, intrarectal and intranasal administrations).

The extracts of the present invention may be used either solely or jointly in pharmaceutically effective amounts for treating animals or humans. They may also be used in pharmaceutically effective amounts in combination with pharmaceutically effective amounts of other pharmaceutically active components in pharmaceutical compositions or preparations.

In the case of preparations for oral administration, one or more of the extracts of the present invention alone or together with commonly-used pharmaceutically acceptable excipients in pharmaceutically acceptable amounts. For example, for oral administration, the extract can be used as a pharmaceutical preparation preferably as is or together with buffers, preservatives, flavors such as saccharides, perfumes, etc. When making the extract dry and into a powder form, the dried powder as is or together with commonly-used excipients such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose, cellulose derivatives, gum arabicum, corn starch, gelatin, etc., (2) disintegrating agents such as corn starch, potato starch, potassium carboxymethylcellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

In the case of parenteral administration using injections, for example, it is possible to prepare solutions or suspensions of one or more extracts of the present invention in pharmaceutically acceptable carriers such as aqueous and nonaqueous solvents such as distilled water for injection, physiological saline solution, Ringer's solution, plant oil, synthetic fatty acid glycerides, higher fatty acid esters, propylene glycol, etc.

It is also possible, depending upon the type of the disease, to prepare pharmaceutical preparations other than the above-mentioned ones such as suppositories, inhalations, aerosol preparations, collyriums, ointments, poultices, etc.

For example, suppositories may be prepared by mixing at least one extract of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of inhalations or aerosol preparations, at least one extract of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

In order to make the extracts of the present invention into collyriums, they can be prepared as a solution or suspension together with an aqueous solvent such as sterile, purified water and physiologically saline solution, or a non-aqueous solvent for injection. The collyriums may also include pharmaceutically acceptable preservants, sterilizing agents, pH adjusting agents, and the like.

The present invention will now be further illustrated by way of the following non-limiting examples wherein all parts, percentages, and ratios are by weight, all temperatures are in ° C. or room temperature, and all pressures are in psia or atmospheric unless otherwise indicated:

EXAMPLE A

Standardization Tests

Standardization tests used to characterize and evaluate the pharmaceutical effectiveness of extracts of crude drugs in accordance with the present invention are a Quantitative Test, an Activity Test, and Confirmation Tests:

I. Quantitative Determination of the Soluble Silicon Compounds ("Quantitative Test")

Water was added to dry powder of a crude drug extract (to an extent of 1 mg/mL), the mixture was stirred at room temperature for ten minutes, subjected to an ultrasonic treatment at room temperature for ten minutes and filtered through a membrane filter (0.45 μm) to remove the insoluble matters, and the filtrate was used as a sample solution to be tested. To 3 mL of this sample solution was added 0.2 mL of sodium hydroxide solution (1 mol/L), the mixture was allowed to stand overnight and 0.3 mL of hydrochloric acid (1 mol/L) was added thereto. After that, 0.1 mL of ammonium molybdate solution (prepared by thorough mixing of 15 g of ammonium molybdate tetrahydrate with 64 mL of a ten-fold diluted aqueous solution of hydrochloric acid to dissolve it, followed by adding water thereto to make 200 mL) was added thereto and mixed therewith. The mixture was allowed to stand for five minutes, mixed with 0.4 mL of an aqueous solution of tartaric acid (170 g/L) and, after one minute, colored by mixing with 0.1 mL of a 1-amino-2-naphthol-4-sulfonic acid solution (prepared by dissolving 1.4 g of sodium sulfite anhydride, 0.3 g of 1-amino-2-naphthol-4-sulfonic acid and 18 g of sodium hydrogen sulfite in water to make 200 mL). After allowing to stand for about 30 minutes, the absorbance at 820 nm wave length was measured so that quantitative determination of silicon was conducted. In the following Examples, the result (μg/mL) is given under the abbreviation "Quantitative Test".

II. Inhibiting Action Against Plasma Kallikrein Production ("Activity Test")

Inhibiting action of the crude drug extract of the present invention against the production of plasma kallikrein was measured according to a method described in the literature [Kiso to Rinsho, volume 20, no. 17, pages 399–405 (1986)].

Thus, a kaolin suspension was added to normal human plasma diluted with a physiological saline solution. After a certain time, lima bean trypsin inhibitor was added to cease the kallikrein production reaction. After that, the substance to be tested is made to coexist in the system where the resulting kallikrein was to be measured using a synthetic substrate (D-Pro-Phe-Arg-p-nitroaniline) whereby the inhibiting activity of said substance to be tested against the kallikrein production was determined. Absorbance at 405 nm was measured using the amount of p-nitroaniline liberated from the synthetic substrate by the produced kallikrein as an index. The potency of the inhibiting activity was expressed as the difference between the absorbance where the substance to be tested was added as above and that where it was not added (control). Thus, the greater the difference ($\Delta OD$) between the absorbances, the greater is the inhibiting activity against the production of kallikrein. When the substance to be tested had a very strong inhibiting activity, the test was conducted using a sample solution where the above test sample (1 mg/mL) was diluted to an appropriate extent. Also, the result calculated for the activity potency of the original sample concentration based upon the degree of dilution was given. In the following examples, the result ($\Delta OD$) is given under the abbreviation "Activity Test".

III. Confirmation Tests of the Components Contained in the Crude Drug Extract ("Confirmation Tests" 1 through 13)

Test (1): Detection of Pentoses (by an orcinol-ferric chloride method)

Sample solution: Crude drug extract (0.1 g) was dissolved in 10 mL of water.

Standard solution: D-Ribose (0.1 mg) was dissolved in 1 mL of water.

Operation: To a sample solution and 1 mL of a standard solution were added 3 mL of a ferric chloride solution and 0.3 mL of an ethanolic solution of orcinol followed by thorough stirring. When the mixture was heated for 25 minutes on a water bath and cooled in running water, the solution gave a green color.

Coloring reagents: a) Ferric chloride (0.1 mg) was dissolved in 100 mL of hydrochloric acid; b) Orcinol (0.1 mg) was dissolved in 100 ml of ethanol.

Test (2): Detection of Hexoses (by an anthrone-sulfuric acid method)

Sample solution: Crude drug extract (0.1 g) was dissolved in 10 mL of water.

Standard solution: D-Glucose (0.1 mg) was dissolved in 1 mL of water.

Operation: Ice-cooled anthrone-sulfuric acid (5 mL) was added to and mixed with an ice-cooled sample solution and the standard solution (1 mL). When the mixture was heated for ten minutes on a water bath and cooled in running water, the solution gave a green color.

Coloring solution: Anthrone (0.2 g) was dissolved in 100 mL of ice-cooled sulfuric acid and the solution was added to 20 mL of water with ice-cooling.

Test (3): Detection of Steroids/Saponins (by a Liebermann's reaction)

Operation: To 0.1 g of a crude drug extract was added 2 mL of acetic anhydride, the mixture was thoroughly stirred, heated for two minutes on a water bath, allowed to stand at room temperature. When 2 mL of sulfuric acid was gently added to 0.7 mL of a supernatant acetic anhydride layer, the interface gave a red to reddish brown color or the upper layer gave a blue to green color.

Test (4): Detection of Carboxyl Group-Containing Compounds (by 2,4-dinitrophenylhydrazine)

Sample solution: To 0.1 g of a crude drug extract was added 3 mL of ethanol, the mixture was thoroughly stirred and allowed to stand and the supernatant liquid was used as a sample solution.

Standard solution: Anisaldehyde (10 mg) was dissolved in 3 mL of an anhydrous ethanol to prepare a standard solution.

Operation: A 2,4-dinitrophenylhydrazine solution (1 mL) was added to a sample solution and a standard solution and, when they were mixed and allowed to stand, the mixture gave a precipitate which was yellow to orange in color.

Reagent: 2,4-Dinitrophenylhydrazine (1.5 g) was dissolved in a cooled mixture of 10 mL of sulfuric acid and 10 mL of water and then water was added thereto to make 100 mL.

Test (5): Detection of Phenol Group-Containing Compounds (by a ferric chloride method)

Sample solution: To 0.1 g of a crude drug extract was added 3 mL of an anhydrous ethanol, the mixture was thoroughly mixed and allowed to stand and the supernatant liquid was used as a sample solution.

Operation: To 1 mL of the sample solution was added 1 mL of a diluted ferric chloride solution and, after the mixture was stirred, the solution gave a blue color.

Reagent: Diluted, ferric chloride (9 g) was dissolved in water and then water was added to 2 mL of the resulting solution to make 10 mL.

Test (6): Confirmation of Flavonoids

Sample solution: To 50 mg of a crude drug extract was added 10 mL of methanol, the mixture was gently heated for 2–3 minutes and centrifuged, then 0.1 g of magnesium ribbons and 1 mL of hydrochloric acid were added to the supernatant liquid and, when the mixture was allowed to stand, the liquid gave a red color.

Test (7): Aldehydes and Ketones (by 2,4-dinitrophenylhydrazine)

Sample solution: To 0.05 g of a crude drug extract was added 1 mL of diluted ethanol, the mixture was thoroughly mixed and allowed to stand, and the supernatant liquid was used as a sample solution.

Developing solvent: an upper layer of n-butanol-acetic acid-water (4:1:5)

Thin layer plate: silica gel (Merck 5553)

Amount of the Sample: 5 $\mu$L

Coloring reagent: 2,4-Dinitrophenylhydrazine (0.4 g) was dissolved in 2 N hydrochloric acid to make 100 mL. After the sample solution was developed and the coloring reagent was sprayed thereon and allowed to stand, it gave a yellow to brown color.

Test (8): Terenes/steroids/saccharides (by anisaldehyde)

Sample solution: To 0.05 g of a crude drug extract was added 1 mL of diluted ethanol, the mixture was thoroughly mixed and allowed to stand, and the supernatant liquid was used as a sample solution.

Developing solvent: an upper layer of n-butanol-acetic acid-water (4:1:5)

Thin layer plate: silica gel (Merck 5553)

Amount of the Sample: 5 $\mu$L

Coloring reagent: To 0.5 mL of p-anisaldehyde was added 1 mL of sulfuric acid followed by adding ethanol thereto to make 20 mL. After the sample solution was developed, the coloring reagent was sprayed thereon and, when heated at 105° C. for five minutes, it gave a blue to purple color and a gray to black color.

Test (9): Amine/indole derivatives (by p-dimethylaminobenzaldehyde)

Sample solution: To 0.05 g of a crude drug extract was added 1 mL of diluted ethanol, the mixture was thoroughly mixed and allowed to stand and the supernatant liquid was used as a sample solution.

Developing solvent: an upper layer of n-butanol-acetic acid-water (4:1:5)

Thin layer plate: silica gel (Merck 5553)

Amount of the Sample: 5 $\mu$L

Coloring reagent: p-Dimethylaminobenzaldehyde (1 g) was dissolved in 50 mL of hydrochloric acid and then 50 mL of ethanol was added thereto. After developing the sample solution, the coloring solution was sprayed thereon followed by allowing it to stand whereupon it gave a blue to purple color.

Test (10): Detection of Tertiary Amines (by a Dragendorff's reagent)

Sample solution: To 0.05 g of a crude drug extract was added 1 mL of ethanol, the resulting dispersion was treated with ultrasonic waves for 30 minutes and heated at 60° C. for five minutes to obtain an extract. The extract was centrifuged and the supernatant liquid was used as a sample solution.

Developing solvent:

a) an upper layer of n-butanol-acetic acid-water (4:1:5)

b) methanol

Thin layer plate: silica gel 60F254

Amount of the Sample: 5 $\mu$L

Coloring reagent: prepared according to the Japanese Pharmacopoeia (13th edition).

Operation: The sample solution was developed, sprayed with a coloring solution and allowed to stand to give a yellow to orange color.

Test (11): Alkaloids (by a platinum chloride-potassium iodide solution)

Sample solution: To 0.05 g of a crude drug extract was added 1 mL of ethanol and the resulting dispersion was treated with ultrasonic waves for 30 minutes and heated at 60° C. for five minutes to obtain an extract. The extract was centrifuged and the supernatant liquid was used as a sample solution.

Developing solvent:

a) an upper layer of n-butanol-acetic acid-water (4:1:5)

b) methanol

Thin layer plate: silica gel 60F254

Amount of the Sample: 5 $\mu$L

Coloring reagent: prepared according to the Japanese Pharmacopoeia (13th edition).

Operation: The sample solution was developed, sprayed with a coloring solution and allowed to stand to give a reddish brown color.

Test (12): Substances Colored with Antimony Trichloride

Sample solution: To 100 mg of a crude drug extract was added 2 mL of 50% ethanol, the mixture was gently heated for 2–3 minutes and centrifuged and the supernatant liquid was used as a sample solution.

Developing solvent:

a) n-propanol-water (64:36)

b) n-hexan-ethyl acetate (3:7)

Thin layer plate: silica gel with fluorescence indicator (UV=365 nm)

Amount of the Sample: 3 $\mu$L

Coloring reagent: prepared according to the Japanese Pharmacopoeia (13th edition).

Operation: The sample solution was developed and, when the coloring solution was sprayed thereon, a blue color resulted.

Test (13): Substances Colored with Ninhydrin

Sample solution: A crude drug extract (0.1 g) was dissolved in 10 mL of water.

Developing solvent: an upper layer of n-butanol-acetic acid-water (4:1:5)

Thin layer plate: silica gel (Merck 5553)

Amount of the Sample: 5 µL

Coloring reagent: prepared according to the Japanese Pharmacopoeia (13th edition).

Operation: The sample solution was developed and, when the coloring solution was sprayed thereon, a blue to purple color resulted.

EXAMPLE 1

In this example, four different manufacturing or extraction methods as described above were used to prepare four crude drug extracts which were then characterized and evaluated in accordance with the present invention:

1) A crude drug extract was prepared according to manufacturing or extraction method 1 above. Thus, to 150 g of shireishi (*Ganoderma lucidum*) was added 3 L of pure water, the mixture was boiled with stirring to obtain an extract, the extract was concentrated in vacuo to about 800 mL and the concentrate was pulverized by spray-drying.

(Quantitative Test) 0.650 µg/mL (Activity Test) 0.772

(Confirmation Test) positive for (3), (4), (7), (8), (9), (10), (11), (12) and (13)

2) A crude drug extract was prepared according to manufacturing or extraction method 2 above. Thus, to 150 g of shireishi (*Ganoderma lucidum*) was added 3 L of pure water and the mixture was boiled with stirring to obtain an extract. To the residue was added 3 L of pure water, the mixture was adjusted to pH 9.5 and boiled with stirring for one hour to extract, the extract was adjusted to pH 7.0, combined with the previously-prepared extract, the combined extract was concentrated in vacuo to about 800 mL and the concentrate was pulverized by spray-drying.

(Quantitative Test) 0.737 µg/mL (Activity Test) 1.440

(Confirmation Test) positive for (3), (4), (7), (8), (9), (10), (11), (12) and (13)

3) A crude drug extract was prepared according to manufacturing or extraction method 3 above. Thus, to 150 g of shireishi (*Ganoderma lucidum*) was added 3 L of an aqueous phenol, the mixture was boiled with stirring for one hour to obtain an extract, the extract was concentrated in vacuo to about 800 mL and the concentrate was pulverized by spray-drying.

(Quantitative Test) 0.682 µg/mL (Activity Test) 0.608

(Confirmation Test) positive for (3), (4), (7), (8), (9), (10), (11), (12) and (13)

4) A crude drug extract was prepared according to manufacturing or extraction methods 5 and 3 above. Thus, to 150 g of shireishi (*Ganoderma lucidum*) was added 3 L of an aqueous phenol, the mixture was boiled with stirring for one hour to obtain an extract, the extract was adjusted to pH 8.5 and concentrated in vacuo to about 800 mL and the concentrate was adjusted to 7.0 and pulverized by spray-drying.

(Quantitative Test) 0.627 µg/mL (Activity Test) 0.824

(Confirmation Test) positive for (3), (4), (7), (8), (9), (10), (11), (12) and (13)

EXAMPLE 2

A crude drug extract was prepared according to manufacturing or extraction methods 5 and 1 above. Thus, to 150 g of creeping saxifrage (*Saxifraga stolonifera*) was added 3 L of pure water and the mixture was boiled with stirring for one hour to obtain an extract. The extract was adjusted to pH 8.5 and concentrated in vacuo to about 800 mL and the concentrate was adjusted to pH 7.0 and pulverized by spray-drying.

(Quantitative Test) 0.388 µg/mL (Activity Test) 1.184

(Confirmation Test) positive for (1), (2), (3), (6), (8), (9), (10), (11), (12) and (13)

EXAMPLE 3

1) The same operations of extraction, concentration and drying as in method 1) of Example 1 were conducted for tanjin (*Salviae militiorrhizae* radix)as a starting crude drug.

(Quantitative Test) 0.304 µg/mL (Activity Test) 1.848

(Confirmation Test) positive for (2), (5), (7), (8), (9), (10), (11), (12) and (13)

2) The same operations of extraction, concentration and drying as in method 2) of Example 1 were conducted for tanjin (*Salviae militiorrhizae* radix) as a starting crude drug.

(Quantitative Test) 0.347 µg/mL (Activity Test) 2.268

(Confirmation Test) positive for (2), (3), (5), (7), (8), (9), (10), (11), (12) and (13)

EXAMPLE 4

1) The same operations of extraction, concentration and drying as in method 1) of Example 1 were conducted for scouring rush (*Equisetum hiemale*) as a starting crude drug.

(Quantitative Test) 2.700 µg/mL (Activity Test) 0.716

(Confirmation Test) positive for (2), (6), (8), (10), (11), (12) and (13)

2) The same operations of extraction, concentration and drying as in method 2) of Example 1 were conducted for scouring rush (*Equisetum hiemale*) as a starting crude drug.

(Quantitative Test) 2.728 µg/mL (Activity Test) 0.876

(Confirmation Test) positive for (2), (6), (8), (9), (10), (11), (12) and (13)

3) The same operations of extraction, concentration and drying as in Example 2 were conducted for scouring rush (*Equisetum hiemale*) as a starting crude drug.

(Quantitative Test) 15.93 µg/mL (Activity Test) 0.996

(Confirmation Test) positive for (2), (6), (8), (9), (10), (11), (12) and (13)

EXAMPLE 5

1) The same operations of extraction, concentration and drying as in method 1) of Example 1 were conducted for Chinese gutta percha as a starting crude drug.

(Quantitative Test) 1.276 µg/mL (Activity Test) 0.688

(Confirmation Test) positive for (2), (4), (7), (8), (9), (10), (11), (12) and (13)

2) The same operations of extraction, concentration and drying as in method 2) of Example 1 were conducted for scouring rush (*Equisetum hiemale*) as a starting crude drug.
(Quantitative Test) 1.805 µg/mL
(Activity Test) 0.880
(Confirmation Test) positive for (2), (3), (4), (7), (8), (9), (10), (11), (12) and (13)

EXAMPLE 6

The same operations of extraction, concentration and drying as in Example 2 were conducted for plantago herb as a starting crude drug.
(Quantitative Test) 0.809 µg/mL
(Activity Test) 0.780
(Confirmation Test) positive for (2), (3), (7), (8), (10), (11), (12) and (13)

EXAMPLE 7

The same operations of extraction, concentration and drying as in method 2) of Example 1 were conducted for plantago seed as a starting crude drug.
(Quantitative Test) 0.392 µg/mL
(Activity Test) 0.752
(Confirmation Test) positive for (2), (4), (5), (7), (8), (9), (10), (11), (12) and (13)

EXAMPLE 8

1) The same operations of extraction, concentration and drying as in method 1) of Example 1 were conducted for chorei (polyporus sclerotium) as a starting crude drug.
(Quantitative Test) 0.725 µg/mL
(Activity Test) 0.189
(Confirmation Test) positive for (2), (3), (7), (8), (10), (12) and (13)
2) The same operations of extraction, concentration and drying as in method 2) of Example 1 were conducted for chorei (polyporus sclerotium) as a starting crude drug.
(Quantitative Test) 0.964 µg/mL
(Activity Test) 0.573
(Confirmation Test) positive for (2), (3), (4), (5), (8), (10), (12) and (13)

EXAMPLE 9

The same operations of extraction, concentration and drying as in method 2) of Example 1 were conducted for saiko (bupleurum root) as a starting crude drug.
(Quantitative Test) 0.281 µg/mL
(Activity Test) 0.434
(Confirmation Test) positive for (2), (3), (8), (9), (10), (11), (12) and (13)

EXAMPLE 10

The same operations of extraction, concentration and drying as in method 2) of Example 1 were conducted for Japanese angelica root as a starting crude drug.
(Quantitative Test) 0.077 µg/mL
(Activity Test) 0.164
(Confirmation Test) positive for (2), (8), (9), (10), (12) and (13)

EXAMPLE 11

1) The same operations of extraction, concentration and drying as in method 3) of Example 1 were conducted for elderberry as a starting crude drug.
(Quantitative Test) 0.203 µg/mL
(Activity Test) 0.090
(Confirmation Test) positive for (2), (3), (8), (9), (10), (11), (12) and (13)
2) The same operations of extraction, concentration and drying as in method 4) of Example 1 were conducted for elderberry as a starting crude drug.
(Quantitative Test) 0.227 µg/mL
(Activity Test) 0.063
(Confirmation Test) positive for (2), (3), (8), (9), (10), (11), (12) and (13)

EXAMPLE 12

1) The same operations of extraction, concentration and drying as in method 1) of Example 1 were conducted for bukuryo (poria sclerotium) as a starting crude drug.
(Quantitative Test) 0.969 µg/mL
(Activity Test) 0.055
(Confirmation Test) positive for (2), (3), (4), (7), (8), (12) and (13)
2) The same operations of extraction, concentration and drying as in method 2) of Example 1 were conducted for bukuryo (poria sclerotium) as a starting crude drug.
(Quantitative Test) 1.711 µg/mL
(Activity Test) 0.084
(Confirmation Test) positive for (2), (3), (4), (8), (10), (11), (12) and (13)

EXAMPLE 13

1) The same operations of extraction, concentration and drying as in method 1) of Example 1 were conducted for pueraria root as a starting crude drug.
(Quantitative Test) 0.118 µg/mL
(Activity Test) 0.071
(Confirmation Test) positive for (2), (3), (5), (6), (8), (9), (10), (11), (12) and (13)
2) The same operations of extraction, concentration and drying as in method 2) of Example 1 were conducted for pueraria root as a starting crude drug.
(Quantitative Test) 0.122 µg/mL
(Activity Test) 0.078
(Confirmation Test) positive for (2), (3), (5), (6), (8), (10), (11), (12) and (13)

EXAMPLE 14

The same operations of extraction, concentration and drying as in method 1) of Example 1 were conducted for crude aloe as a starting crude drug.
(Quantitative Test) 0.536 µg/mL
(Activity Test) 0.074
(Confirmation Test) positive for (2), (5), (8), (12) and (13)

EXAMPLE 15

The same operations of extraction, concentration and drying as in method 1) of Example 1 were conducted for ginseng as a starting crude drug.
(Quantitative Test) 0.087 µg/mL
(Activity Test) 0.051
(Confirmation Test) positive for (2), (3), (4), (7), (8), (10), (11), (12) and (13)

A summary of the results of analysis and evaluation of each of the extracts of Examples 1 through 15 is given in Table 1 where "p" indicates a positive result and no entry indicates a negative result for the confirmation test:

TABLE 1

SUMMARY OF RESULTS OF ANALYSIS AND PHARMACEUTICAL ACTIVITY OF CRUDE DRUG EXTRACTS

| EXAMPLE | EXTRACTION METHOD | QUANTITATIVE TEST μgSi/ml | ACTIVITY TEST | CONFIRMATION TEST | | | | | | | | | | | | |
|---|---|---|---|---|---|---|---|---|---|---|---|---|---|---|---|---|
| | | | | 1 | 2 | 3 | 4 | 5 | 6 | 7 | 8 | 9 | 10 | 11 | 12 | 13 |
| 1-1 | 1 | 0.65 | 0.772 | | | p | p | | | p | p | p | p | p | p | p |
| 1-2 | 2 | 0.737 | 1.44 | | | p | p | | | p | p | p | p | p | p | p |
| 1-3 | 3 | 0.682 | 0.608 | | | p | p | | | p | p | p | p | p | p | p |
| 1-4 | 5(3) | 0.627 | 0.824 | | | p | p | | | p | p | p | p | p | p | p |
| 2 | 5(1) | 0.388 | 1.184 | p | p | p | | | p | | p | p | p | p | p | p |
| 3-1 | 1 | 0.304 | 1.848 | | p | | | p | | p | p | p | p | p | p | p |
| 3-2 | 2 | 0.347 | 2.268 | | p | p | | p | | p | p | p | p | p | p | p |
| 4-1 | 1 | 2.7 | 0.716 | p | | | | | p | | p | | p | p | p | p |
| 4-2 | 2 | 2.728 | 0.876 | p | | | | | p | | p | p | p | p | p | p |
| 4-3 | 5(1) | 15.93 | 0.996 | p | | | | | p | | p | p | p | p | p | p |
| 5-1 | 1 | 1.276 | 0.688 | p | | p | | | | p | p | p | p | p | p | p |
| 5-2 | 2 | 1.805 | 0.88 | p | p | p | | | | p | p | p | p | p | p | p |
| 6 | 5(1) | 0.809 | 0.78 | p | p | | | | | p | p | | p | p | p | p |
| 7 | 2 | 0.392 | 0.752 | p | | p | p | | | p | p | p | p | p | p | p |
| 8-1 | 1 | 0.725 | 0.189 | p | p | | | | | p | p | | p | | p | p |
| 8-2 | 2 | 0.964 | 0.573 | p | p | p | p | | | | p | | p | | p | p |
| 9 | 2 | 0.281 | 0.434 | p | p | | | | | | p | p | p | p | p | p |
| 10 | 2 | 0.077 | 0.164 | p | | | | | | | p | p | p | | p | p |
| 11-1 | 3 | 0.203 | 0.09 | p | p | | | | | | p | p | p | p | p | p |
| 11-2 | 5(3) | 0.227 | 0.063 | p | p | | | | | | p | p | p | p | p | p |
| 12-1 | 1 | 0.969 | 0.055 | p | p | p | | | | p | p | | | | p | p |
| 12-2 | 2 | 1.711 | 0.084 | p | p | p | | | | | p | | p | p | p | p |
| 13-1 | 1 | 0.118 | 0.071 | p | p | | p | p | | p | p | p | p | p | p | p |
| 13-2 | 2 | 0.122 | 0.078 | p | p | | p | p | | | p | | p | p | p | p |
| 14 | 1 | 0.536 | 0.074 | p | | | p | | | | p | | | | p | p |
| 15 | 1 | 0.087 | 0.051 | p | p | p | | | | p | p | | p | p | p | p |

It is apparent from the results of the above-mentioned Examples where various crude drugs were used that, when soluble silicon compounds are contained in more than certain amounts, the crude drug extracts exhibit a pharmaceutical effect. The method of the present invention establishes a standardization for crude drugs which has been ambiguous up to now. The silicon compounds contained in the crude drug extracts include various kinds of compounds. In the present invention, they are wholly standardized in terms of amount calculated as silicon measured by a molybdenum blue method. Depending upon the type of the crude drug, substances therein other than the silicon compounds are varied. However, when coloring reaction tests, etc. for such substances are appropriately used together with the silicon content determination, more precise standardization of crude drugs can be established.

As shown in Table 1, the Examples indicate a tendency for an increase in the extracting efficiency of the soluble silicon compounds when the extracting operation is conducted using a solution where the pH is adjusted to an alkaline region (e.g. pH being around 9.5), as for example in extraction method 2. Accordingly, extraction using a solution where the pH is adjusted to the alkaline region (e.g. pH about 9.5) is an example of a preferred extracting method.

As such, in accordance with the present invention, when soluble silicon compounds which provide a pharmaceutical effect, such as inhibition of plasma kallikrein, are used as an index, the quality of various crude drugs and extracts thereof can be standardized. Accordingly, the present invention achieves crude drug extracts having a stable quality and greatly contributes to the appropriate standardization of pharmaceuticals.

What is claimed is:

1. A method for standardizing or evaluating plant drugs for pharmaceutical effectiveness comprising subjecting a plant drug to extraction to obtain an extract solution, drying the extract solution to obtain a dry drug extract, determining the amount of soluble silicon compounds calculated as silicon per gram of dry drug extract, and comparing the determined amount of soluble silicon compounds to a minimal amount needed to obtain inhibition of plasma kallikrein production.

2. A method as claimed in claim 1 wherein the plant drug is subjected to extraction with water or an aqueous solvent to obtain an extract solution and the extract solution is dried to obtain a drug extract in powder form.

3. A method as claimed in claim 2 wherein the pH of said water or aqueous solvent for extraction is adjusted to 8.5 to 10.5.

4. A method as claimed in claim 1 wherein the amount of soluble silicon compounds is determined by a molybdenum blue method.

5. A method as claimed in claim 1 wherein the amount of soluble silicon is determined by dissolving the dry drug extract, removing insoluble matter to obtain a filtrate, admixing the filtrate with ammonium molybdate tetrahydrate, and measuring absorbance at a wavelength of 820 nm.

6. A method as claimed in claim 1 wherein the standardization or evaluation further comprises measuring inhibiting action of the drug extract against plasma kallikrein production.

7. A method as claimed in claim 1 wherein the standardization or evaluation further comprises subjecting said drug extract to a plurality of coloring reactions.

8. A method for standardizing plant drug extracts comprising determining the amount of soluble silicon compounds calculated as silicon per gram of dry drug extract, measuring inhibiting action of the drug extract against plasma kallikrein production, and subjecting said drug extract to a plurality of coloring reactions.

9. A method as claimed in claim 8 wherein said plant drug extracts are obtained by subjecting a plant drug to extraction with water or an aqueous solvent to obtain an extract solution and the extract solution is dried to obtain a drug extract in powder form.

10. A method as claimed in claim 9 wherein the pH of said water or aqueous solvent for extraction is adjusted to 8.5 to 10.5.

11. A method as claimed in claim 8 wherein the amount of soluble silicon is determined by dissolving the dry drug extract in water to an extent of 1 mg/mL, removing insoluble matter to obtain an aqueous solution, and determining the amount of the silicon in said aqueous solution.

12. A method as claimed in claim 11 wherein the drug extracts are standardized for pharmaceutical effectiveness as an anti-allergic agent, an analgesic agent, or an anti-inflammatory agent.

13. A method for evaluating the inhibiting activity of plant drug extracts against plasma kallikrein production comprising:

determining the amount of soluble silicon compounds calculated as silicon per gram of dry drug extract; and comparing the determined amount of soluble silicon compounds to a minimal amount needed to obtain inhibition of plasma kallikrein production.

* * * * *